(12) United States Patent
Rousseau

(10) Patent No.: US 12,222,358 B2
(45) Date of Patent: Feb. 11, 2025

(54) DRIVE DEVICE FOR AN AUTOMATIC ANALYSIS APPARATUS FOR IN VITRO DIAGNOSTICS

(71) Applicant: ARTEION, Paris (FR)

(72) Inventor: Alain Rousseau, Paris (FR)

(73) Assignee: ARTEION, Paris (FR)

( * ) Notice: Subject to any disclaimer, the term of this patent is extended or adjusted under 35 U.S.C. 154(b) by 477 days.

(21) Appl. No.: 17/010,555

(22) Filed: Sep. 2, 2020

(65) Prior Publication Data

US 2021/0063426 A1 Mar. 4, 2021

(30) Foreign Application Priority Data

Sep. 4, 2019 (FR) ..................... 19/09741

(51) Int. Cl.
*G01N 35/04* (2006.01)
*G01N 35/02* (2006.01)

(52) U.S. Cl.
CPC ........... *G01N 35/04* (2013.01); *G01N 35/021* (2013.01); *G01N 35/026* (2013.01); *G01N 2035/0401* (2013.01); *G01N 2035/0408* (2013.01); *G01N 2035/0412* (2013.01); *G01N 2035/0484* (2013.01)

(58) Field of Classification Search
CPC .... G01N 35/021; G01N 35/026; G01N 35/04; G01N 2035/0401; G01N 2035/0408; G01N 2035/023; G01N 2035/0484; G01N 2021/0378; G01N 33/4905
See application file for complete search history.

(56) References Cited

U.S. PATENT DOCUMENTS

| 5,008,082 A * | 4/1991 | Shaw ..................... G01N 35/04 422/549 |
| 5,769,791 A * | 6/1998 | Benaron ............ A61B 17/3417 600/476 |
| 7,678,332 B2 | 3/2010 | Rousseau et al. |
| 7,959,878 B2 | 6/2011 | Rousseau |
| 10,605,801 B2 | 3/2020 | Rousseau et al. |
| 2009/0120769 A1* | 5/2009 | Rousseau ............. G01N 35/026 198/844.1 |

(Continued)

FOREIGN PATENT DOCUMENTS

| EP | 3178556 A1 | 6/2017 |
| FR | 2835617 A1 | 8/2003 |

(Continued)

OTHER PUBLICATIONS

French Search Report for Application No. 19/09741.

*Primary Examiner* — P. Kathryn Wright
*Assistant Examiner* — Curtis A Thompson
(74) *Attorney, Agent, or Firm* — CANTOR COLBURN LLP

(57) ABSTRACT

The drive device includes a guide element defining a guide track, the guide element being configured to receive and guide a cuvettes strip in translation along the guide track, and a drive belt configured to displace the cuvettes strip in translation along the guide track when the cuvettes strip is received in the guide element. The drive belt is disposed below the guide track and is configured to cooperate with lower portions of the cuvettes of the cuvettes strip when the cuvettes strip is received in the guide element.

12 Claims, 5 Drawing Sheets

(56) References Cited

U.S. PATENT DOCUMENTS

| | | | |
|---|---|---|---|
| 2014/0090957 A1* | 4/2014 | Yamauchi | B65G 47/52 198/418.5 |
| 2014/0268163 A1* | 9/2014 | Milner | A61B 6/03 356/451 |
| 2017/0176255 A1* | 6/2017 | Nciri | G01J 3/0224 |
| 2017/0370905 A1* | 12/2017 | Rousseau | G01N 33/4905 |
| 2018/0059006 A1* | 3/2018 | Fritchie | G01N 21/27 |
| 2018/0369806 A1 | 12/2018 | Behnk | |
| 2019/0242822 A1* | 8/2019 | Ma | C12Q 1/686 |

FOREIGN PATENT DOCUMENTS

| | | |
|---|---|---|
| FR | 3030048 A1 | 6/2016 |
| JP | 2000009737 | 1/2000 |
| WO | 2007085715 A1 | 8/2007 |

\* cited by examiner

DRIVE DEVICE FOR AN AUTOMATIC ANALYSIS APPARATUS FOR IN VITRO DIAGNOSTICS

CROSS REFERENCE TO RELATED APPLICATIONS

This application claims priority under 35 U.S.C. § 119 to the following French Patent Application No. FR 19/09741, filed on Sep. 4, 2019, the entire contents of which are incorporated herein by reference thereto.

TECHNICAL FIELD

The present invention concerns a drive device for an automatic analysis apparatus for in vitro diagnostics, and an automatic analysis apparatus for in vitro diagnostics comprising such a drive device.

BACKGROUND

The document FR2835617 discloses an automatic analysis apparatus for in vitro diagnostics including in particular:
a cuvettes strip including a plurality of cuvettes secured together by a film, each cuvette comprising a receptacle configured to contain a biological fluid to be analyzed, the receptacle comprising an upper opening and a bottom delimiting a concave raceway whose concavity is directed upwards, the raceway being intended to guide an oscillatory movement of a ferromagnetic bead, each cuvette further including two lateral flanges extending from the respective upper opening and projecting outwards of the respective cuvette,
a drive device comprising a guide element which defines a guide track and which is configured to receive and guide the cuvettes strip in translation along the guide track, and a drive belt configured to displace the cuvettes strip in translation along the guide track, and
a measuring station disposed along the guide track.

More particularly, the drive belt includes an outer notching comprising a plurality of outer notches which are spaced apart along the drive belt, each outer notch being configured to mesh with shapes that are provided on the lateral flanges of the cuvettes and which form a rack.

Such an automatic analysis apparatus has high compactness and allows displacing a plurality of cuvettes simultaneously.

Nonetheless, since the cuvettes are guided and driven in translation at the level of their upper portions, the positioning of the lower portions of the cuvettes, where the measurements are performed, is uncertain, which is not conducive to a proper replicability of the measurement conditions.

In addition, the cuvettes are not vertically guided in an accurate manner with respect to a reference position, which might also affect the replicability of the measurement conditions.

Furthermore, the cuvettes are not mechanically stabilized in a perfect manner in the guide element, such that the introduction of a sampling needle into one of the cuvettes, in order to feed said cuvettes with the biological fluid to be analyzed or with reagents, might cause vibrations in the adjacent cuvettes and therefore instabilities of the movements of the beads received in these adjacent cuvettes, which are likely to affect the reliability of the completed measurements.

BRIEF SUMMARY

Hence, the technical problem underlying the invention consists in providing a drive device that has a simple and economical structure, while significantly improving the reliability of the measurements carried out with an automatic analysis apparatus equipped with such a drive device.

To this end, the present invention concerns a drive device for an automatic analysis apparatus for in vitro diagnostics, the drive device including:
a guide element defining a guide track, which may be rectilinear for example, the guide element being configured to receive and guide a cuvettes strip in translation along the guide track, and
a drive belt configured to displace the cuvettes strip in translation along the guide track when the cuvettes strip is received in the guide element,
wherein the drive belt is disposed below the guide track and is configured to cooperate with lower portions of the cuvettes of the cuvettes strip when the cuvettes strip is received in the guide element.

Thus, the drive belt is configured to be located below the cuvettes strip when the cuvettes strip is received in the guide element.

Such a cooperation of the drive belt with the lower portions of the cuvettes allows ensuring an accurate positioning of the lower portions of the cuvettes at a measuring station, and therefore improving the reliability of the measurements carried out with an automatic analysis apparatus equipped with a drive device according to the present invention.

The drive device may further have one or more of the following features, considered separately or in combination.

According to an embodiment of the invention, the drive belt includes a lower strand and an upper strand which are superimposed.

According to an embodiment of the invention, the drive belt includes an outer notching comprising a plurality of outer notches which are spaced apart along the drive belt, each outer notch being configured to extend between the lower portions of two adjacent cuvettes of the cuvettes strip when the cuvettes strip is received in the guide element.

According to an embodiment of the invention, each outer notch is configured to cooperate with the lower portions of two adjacent cuvettes of the cuvettes strip when the cuvettes strip is received in the guide element.

According to an embodiment of the invention, the pitch between each pair of adjacent outer notches is substantially equal to the pitch between each pair of adjacent cuvettes of the cuvettes strip.

According to an embodiment of the invention, the distance between each pair of adjacent outer notches is substantially equal to the width of the cuvettes of the cuvettes strip.

According to an embodiment of the invention, the drive device includes two rotary support members configured to support the drive belt, the two rotary support members having axes of rotation which extend substantially horizontally, and in particular when an automatic analysis apparatus equipped with the drive device according to the present invention is positioned on a planar and horizontal support.

According to an embodiment of the invention, one of the rotary support members is a drive wheel and the other one of the rotary support members is a driven wheel.

According to an embodiment of the invention, the drive belt includes an inner notching comprising a plurality of inner notches which are spaced apart along the drive belt, the inner notches being configured to mesh with toothings provided on at least one of the rotary support members, and for example on the drive wheel.

According to an embodiment of the invention, the guide element includes a lower opening emerging in the guide track and through which an upper strand of the drive belt extends.

According to an embodiment of the invention, the drive device includes a covering element which is fastened to the guide element and which covers at least partially the guide track.

According to an embodiment of the invention, the drive device includes at least one upper stop surface which is located above the guide track and against which an upper face of the cuvettes strip is adapted to bear when the cuvettes strip is received in the guide element.

Such a configuration of the drive device allows reducing the vertical mechanical clearance of the cuvettes by sandwiching the cuvettes strip between the drive belt and the at least one upper stop surface, which improves the vertical positioning of the cuvettes in particular at a measuring station, and therefore the reliability of the measurements carried out by the measuring station.

According to an embodiment of the invention, the at least one stop surface is provided on the covering element.

According to an embodiment of the invention, the covering element comprises at least one stop rib which includes the at least one upper stop surface. Advantageously, the covering element comprises two stop ribs which are substantially parallel and each including an upper stop surface.

According to an embodiment of the invention, the drive device includes a bearing device which is located below the guide track and which is configured to exert a bearing force against a belt portion of the drive belt such that, when the cuvettes strip is received in the guide element, the cuvettes located opposite the belt portion are pressed by the belt portion against the at least one upper stop surface.

Such a configuration of the drive device allows mechanically uncoupling the cuvettes from one another and mechanically stabilizing the cuvettes in the guide element, and in particular at a measuring station, such that the introduction of a sampling needle into one of the cuvettes, in order to feed said cuvette with the biological fluid to be analyzed or with reagents, is not likely to cause vibrations in the adjacent cuvettes and therefore affecting the reliability of the measurements carried out in the adjacent cuvettes.

Furthermore, such a configuration of the drive device allows holding the cuvettes in abutment against the at least one upper stop surface during their displacements in the guide track, and that in particular at a measuring station. This results in an improvement in the positioning of the lower portions of the cuvettes, and therefore in the reliability of the completed measurements.

According to an embodiment of the invention, the bearing device is configured to exert a bearing force against the upper strand of the drive belt.

According to an embodiment of the invention, the bearing force is directed transversely, and for example perpendicularly, to the guide track.

According to an embodiment of the invention, the guide element has a U-shaped cross-section.

According to an embodiment of the invention, the guide element includes two lateral guide walls which are substantially vertical and which laterally delimit the guide track.

According to an embodiment of the invention, the guide element includes two upper guide faces each extending along a respective lateral guide wall.

The present invention further concerns an automatic analysis apparatus for in vitro diagnostics, including a drive device according to the present invention, a cuvettes strip received in the guide element and a measuring station disposed along the guide track.

According to an embodiment of the invention, the cuvettes strip includes a plurality of cuvettes, each cuvette comprising a receptacle configured to contain a biological fluid to be analyzed, such as a blood sample, the receptacle comprising an upper opening and a bottom delimiting a raceway which is concave and whose concavity is directed upwards, the raceway being intended to guide an oscillatory movement of a ferromagnetic bead.

According to an embodiment of the invention, each cuvette is made of a plastic material transparent to the light beams.

According to an embodiment of the invention, each cuvette includes two lateral flanges extending from the upper opening and projecting outwards of the cuvette. Advantageously, each lateral flange of each cuvette includes a protrusion, for example cylindrical, extending opposite to the respective receptacle.

According to an embodiment of the invention, the cuvettes of the cuvettes strip are secured together by a film. Advantageously, the film covers at least partially the upper openings of the cuvettes of the cuvettes strip.

According to an embodiment of the invention, the film of the cuvettes strip includes a first series of holes formed along a first longitudinal edge of the film and a second series of holes formed along a second longitudinal edge of the film, the protrusions of each cuvette being respectively fitted into a hole of the first series of holes and into a hole of the second series of holes.

According to an embodiment of the invention, the film includes a plurality of passage holes each emerging in the upper opening of a respective cuvette.

According to an embodiment of the invention, each cuvette is fastened to the film in a detachable manner.

According to an embodiment of the invention, the lateral flanges of the cuvettes of the cuvettes strip are intended to rest on the guide element, and for example, on the two upper guide faces of the guide element.

According to an embodiment of the invention, the bearing device is located at the measuring station.

According to an embodiment of the invention, the covering element includes a plurality of passage openings configured to be located opposite upper openings of the cuvettes when the cuvettes strip is received in the guide element.

According to an embodiment of the invention, the measuring station is configured to determine times for modification of the physical state of a biological fluid to be analyzed contained in a cuvette of the cuvettes strip.

According to an embodiment of the invention, the measuring station includes at least one measuring unit configured to determine a coagulation time of a blood sample contained in a cuvette of the cuvettes strip that is located at the at least one measuring unit, the at least one measuring unit comprising:
  a magnetic field generation system configured to generate a magnetic field adapted to displace a ferromagnetic bead, received in the cuvette located at the at least one measuring unit, along the raceway and according to an oscillatory movement,
  an emission device configured to emit an incident light beam in the direction of the blood sample contained in the cuvette located at the at least one measuring unit, the incident light beam being configured to be at least partially concealed by the ferromagnetic bead over at least one portion of the movement of the ferromagnetic bead along the raceway, and a detection element configured to detect at least one light beam that is transmitted through the cuvette located at the at least one measuring unit and which is derived from the incident light beam, and to output a measurement signal.

According to an embodiment of the invention, the magnetic field generation system includes two electromagnets disposed on either side of the guide track.

According to an embodiment of the invention, the magnetic field generation system includes a setting unit which is configured to set the durations of the current pulses applied to the two electromagnets according to the tests to be carried out.

According to an embodiment of the invention, the emission device and the detection element are disposed on either side of the guide track, and are thus configured to be disposed on either side of the cuvettes strip when the cuvettes strip is received in the guide element.

According to an embodiment of the invention, the emission device and the detection element are disposed substantially in the axis of the raceway of the cuvette of the cuvettes strip which are located at the at least one measuring unit.

According to an embodiment of the invention, the detection element is located substantially in the optical axis of the incident light beam.

According to an embodiment of the invention, the emission device includes a plurality of light sources configured to emit light beams with different wavelengths, and a wavelengths multiplexing device configured to mix the light beams with different wavelengths originating from the light sources so as to form a polychromatic light beam, and therefore such that the incident light beam emitted by the emission device is polychromatic. These arrangements allow obtaining a high-power incident light beam with a small diameter.

According to an embodiment of the invention, the wavelengths multiplexing device is configured to collect the light beams with different wavelengths originating from the light sources.

According to an embodiment of the invention, the light sources have substantially horizontal axes.

According to an embodiment of the invention, the light sources are configured to emit monochromatic light beams with different wavelengths.

According to an embodiment of the invention, each light source includes a light-emitting diode and a spectral selection filter disposed in front of the respective light-emitting diode. The use of a light-emitting diode for each light source allows obtaining a high-power light beam within a reduced bulk, with simple control electronics, and easily selecting the wavelengths, according to the measurements to be carried out.

According to an embodiment of the invention, the spectral selection filters are substantially coplanar.

According to an embodiment of the invention, the light sources are shifted with respect to one another according to a shift direction which is transverse to the optical axis of the incident light beam.

According to an embodiment of the invention, the light-emitting diodes are shifted vertically with respect to one another.

According to an embodiment of the invention, the wavelengths multiplexing device includes an optical cavity including a first cavity portion located in the proximity of the light sources and having a first cross-section, and a second cavity portion located in the continuation of the first cavity portion and having a second cross-section which is smaller than the first cross-section.

According to an embodiment of the invention, the first cavity portion and the second cavity portion are disposed coaxially.

According to an embodiment of the invention, the second cross-section of the second cavity portion is circular.

According to an embodiment of the invention, the second cross-section of the second cavity portion has a diameter comprised between 2 and 4 mm.

According to an embodiment of the invention, the second cavity portion is cylindrical.

According to an embodiment of the invention, the first cross-section of the first cavity portion is oblong.

According to an embodiment of the invention, the first cross-section of the first cavity portion is constant along the optical axis of the optical cavity.

According to an embodiment of the invention, the optical cavity has a length comprised between 40 and 70 mm.

According to an embodiment of the invention, the optical cavity includes a third cavity portion which is separate from the second cavity portion by a separating wall including a passage orifice having a section smaller than the second cross-section.

According to an embodiment of the invention, the third cavity portion and the second cavity portion are disposed coaxially.

According to an embodiment of the invention, the passage orifice is centered on the optical axis of the optical cavity.

According to an embodiment of the invention, the emission device further includes a focusing lens, such as a biconvex focusing lens, configured to focus the polychromatic light beam on a focus point located in the guide track, and advantageously in the lower portion of the cuvette of the cuvettes strip that is located at the at least one measuring unit. Advantageously, the focus point, where the polychromatic light beam is focused, is located substantially at the center of the lower portion of the cuvette that is located at the at least one measuring unit, and for example above the respective ferromagnetic bead.

According to an embodiment of the invention, the emission device is configured such that the portion of the incident light beam extending in the guide track is substantially symmetrical on either side of the focus point.

According to an embodiment of the invention, the focusing lens is located at the output of the wavelengths multiplexing device.

According to an embodiment of the invention, the focusing lens is configured to collimate the polychromatic light beam originating from the wavelengths multiplexing device.

According to an embodiment of the invention, the focusing lens is positioned at a distance from the wavelengths multiplexing device which substantially corresponds to a focal distance of the focusing lens.

According to an embodiment of the invention, the ratio between the focal distance of the focusing lens and the distance between the wavelengths multiplexing device and the focusing lens is comprised between 0.8 and 1.2, and for example between 0.8 and 1.

According to an embodiment of the invention, the emission device is configured so that each light beam originating from a light source propagates in free space from the corresponding light source up to the collimating lens.

According to an embodiment of the invention, the light-emitting diodes are fastened to a support member.

According to an embodiment of the invention, the detection element is a photodetector, such as a photodiode.

According to an embodiment of the invention, the at least one measuring unit is configured to carry out photometric measurements, spectrophotometric measurements, and/or fluorescence measurements.

According to an embodiment of the invention, the at least one measuring unit is configured to carry out photometric measurements, and in particular to measure the D-dimers or CRP content in the sample to be analyzed.

According to an embodiment of the invention, the measuring station includes a plurality of measuring units shifted along the guide track. Advantageously, the measuring units are identical.

BRIEF DESCRIPTION OF THE DRAWINGS

Anyway, the invention will be better understood using the following description with reference to the appended schematic drawings representing, as a non-limiting example, an embodiment of this automatic analysis apparatus for in vitro diagnostics.

DETAILED DESCRIPTION

Figure 1:
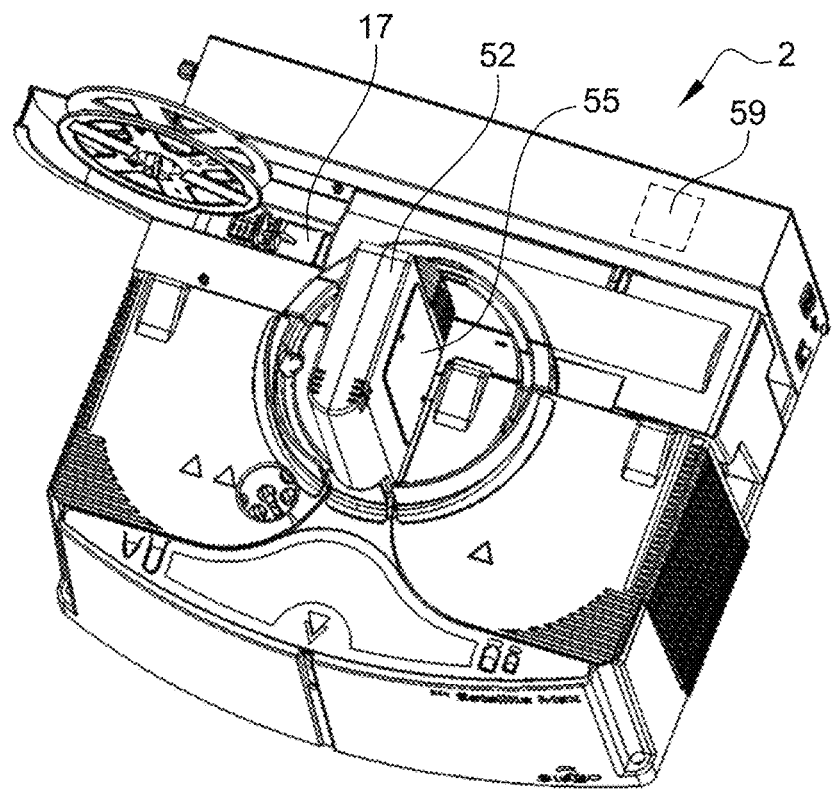
FIG. 1 is a top perspective view of an automatic analysis apparatus according to the present invention.
Figure 2:
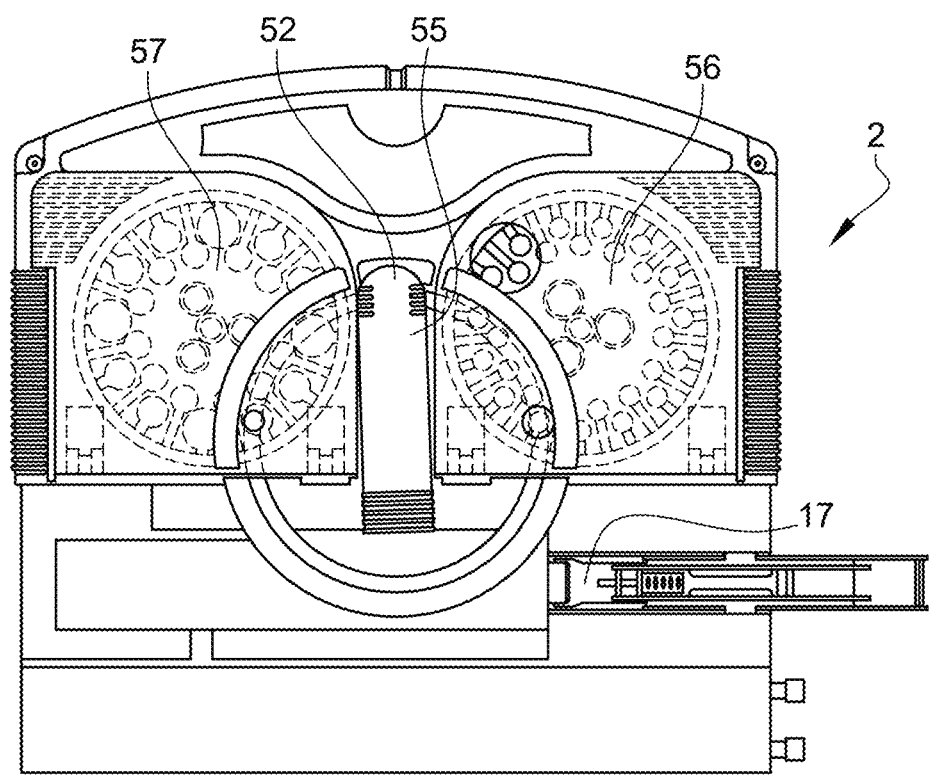
FIG. 2 is a top view of the automatic analysis apparatus of FIG. 1.
Figure 3:
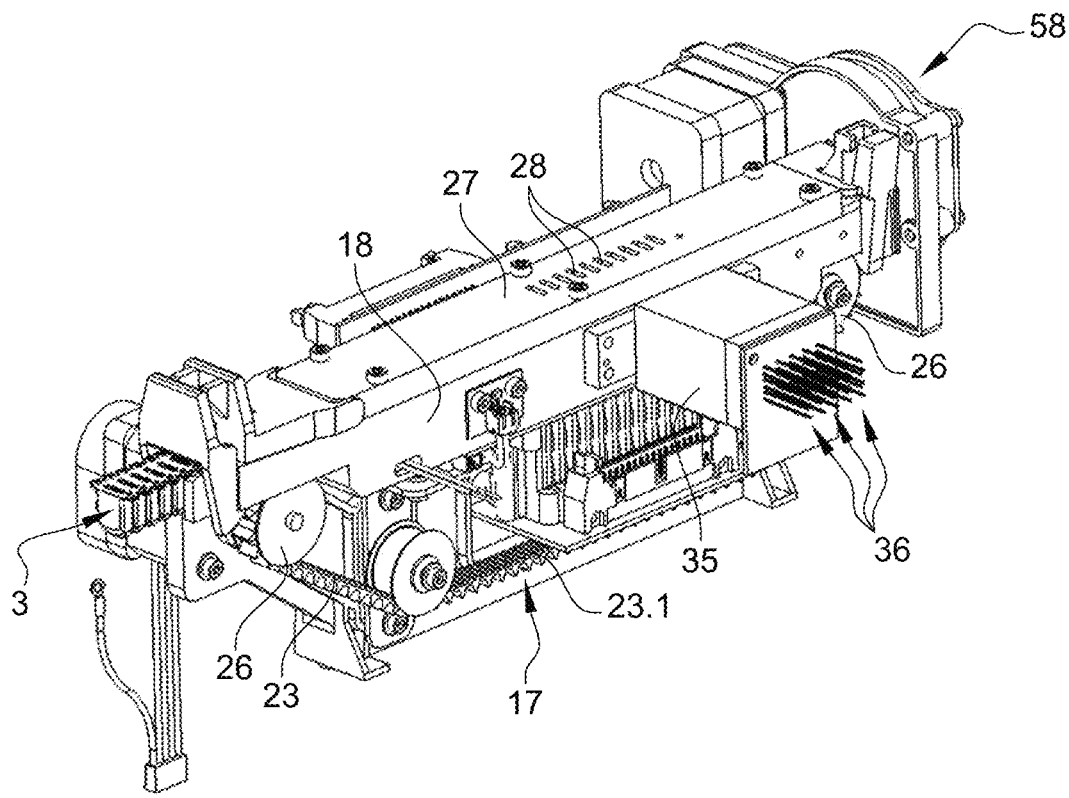
FIG. 3 is a perspective partial view of the automatic analysis apparatus of FIG. 1.
Figure 4:
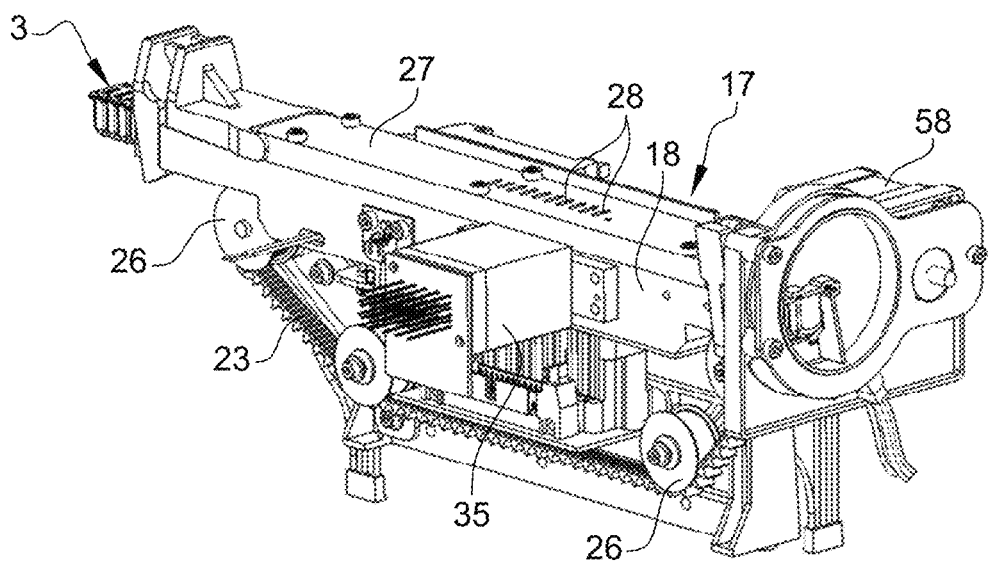
FIG. 4 is a perspective partial view of the automatic analysis apparatus of FIG. 1.
Figure 5:
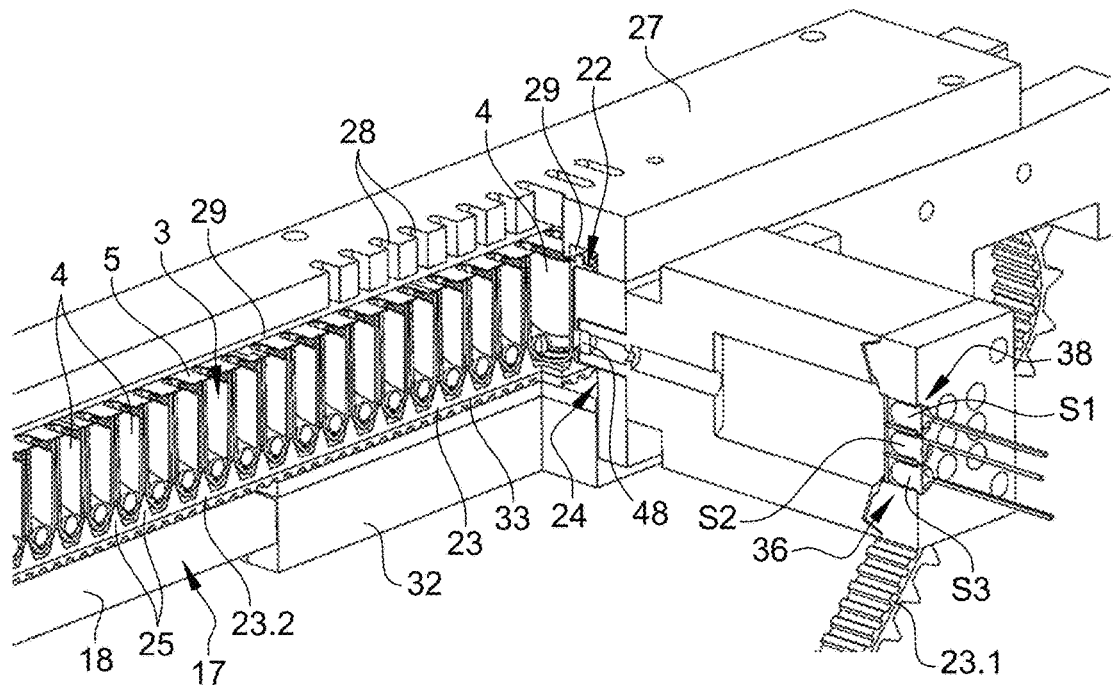
FIG. 5 is a perspective partial view, partially truncated, of the automatic analysis apparatus of FIG. 1.

FIGS. 1 to 10 represent an automatic analysis apparatus 2 for in vitro diagnostics, and more particularly to carry out blood tests.

The automatic analysis apparatus 2 comprises a cuvettes strip 3 (cf. in particular FIG. 9) including a series of cuvettes 4 which are secured together by a film 5. For example, each cuvette 4 may be fastened to the film 5 in a detachable manner.

Advantageously, each cuvette 4 is made by molding of a plastic material transparent to the light beams, and comprises a receptacle 6 configured to contain a biological fluid to be analyzed, such as a blood sample. The receptacle 6 of each cuvette 4 has a generally parallelepiped shape.

The receptacle 6 of each cuvette 4 comprises an upper portion 6.1 comprising an upper opening 7 and a lower portion 6.2 including a bottom 8 delimiting a concave raceway 9 whose concavity is directed upwards. The raceway 9 of each receptacle 6 is intended to guide an oscillatory movement of a ferromagnetic bead 11, and had its lowest point substantially at the center thereof.

Each cuvette 4 further includes two lateral flanges 12 extending from the respective upper opening 7 and projecting outwards of the cuvette 4. Advantageously, each lateral flange 12 of each cuvette 4 includes a protrusion 13, for example cylindrical, extending opposite to the respective receptacle 6.

According to the embodiment represented in the figures, the film 5 is flexible and includes a first series of holes 14 formed along a first longitudinal edge of the film 5 and a second series of holes 15 formed along a second longitudinal edge of the film 5. The protrusions 13 of each cuvette 4 are forcibly fitted respectively into a hole 14 of the first series of holes and into a hole 15 of the second series of holes.

Advantageously, the film 5 partially covers the upper openings 7 of the cuvettes 4, and includes a plurality of passage holes 16 each emerging in the upper opening 7 of a respective cuvette 4.

The automatic analysis apparatus 2 further comprises a drive device 17 including a guide element 18 which defines a guide track 19 and which is configured to receive and guide the cuvettes strip 3 in translation along the guide track 19. Advantageously, the guide track 19 is rectilinear.

The guide element 18 has a U-shaped cross-section, and includes two lateral guide walls 21 which are substantially vertical and which laterally delimit the guide track 19. The guide element 18 further includes two upper guide faces 22 each extending along a respective lateral guide wall 21. More particularly, the lateral flanges 12 of the cuvettes 4 of the cuvettes strip 3 are intended to rest on the two upper guide faces 22 of the guide element 18 when the cuvettes strip 3 is received in the guide element 18.

In addition, the drive device 17 includes a drive belt 23 which is disposed below the guide track 19 and which is therefore configured to be located below the cuvettes strip 3 when the cuvettes strip 3 is received in the guide element 18. The drive belt 23 is an endless belt and more particularly includes a lower strand 23.1 and an upper strand 23.2 which are superimposed. Advantageously, the guide element 18 includes a lower opening 24 emerging in the guide track 19 and through which the upper strand 23.2 of the drive belt 23 extends. The lower opening 24 extends according to the direction of extension of the guide track 19.

The drive belt 23 is configured to displace the cuvettes strip 3 in translation along the guide track 19 when the cuvettes strip 3 is received in the guide element 18. To this end, the drive belt 23 includes an outer notching comprising a plurality of outer notches 25 which are spaced apart along the drive belt 23. For example, each outer notch 25 may have a generally triangular cross-section.

Each outer notch 25 is configured to extend between and cooperate with the lower portions 6.2 of two adjacent cuvettes 4 of the cuvettes strip 3 when the cuvettes strip 3 is received in the guide element 18. Advantageously, the pitch between each pair of adjacent outer notches 25 is substantially equal to the pitch between each pair of adjacent cuvettes 4 of the cuvettes strip 3. Thus, the distance between each pair of adjacent outer notches 25 is substantially equal to the width of the cuvettes 4 of the cuvettes strip 3.

The drive device 17 also includes two rotary support members 26 configured to support the drive belt 23. The two rotary support members 26 have axes of rotation which extend substantially horizontally when the automatic analysis apparatus is positioned on a planar and horizontal support. Advantageously, one of the rotary support members 26 is a drive wheel and the other one of the rotary support members 26 is a driven wheel. For example, the drive wheel is driven in rotation by a drive motor, such as a stepper motor. In addition, each of the rotary support members 26 may be provided with toothings configured to cooperate with an inner notching provided on the drive belt 23.

The drive device 17 further includes a covering element 27 which is fastened to the guide element 18 and which covers the guide track 19 over substantially the entire length of the guide track 19.

The covering element 27 includes a plurality of passage openings 28 configured to be located opposite upper openings 7 of the cuvettes 4 when the cuvettes strip 3 is received in the guide element 18. Each passage opening 28 is intended for the passage of a sampling needle which will be described in more details hereinafter.

The covering element 27 also includes, on its inner face turned towards the guide element 18, two stop ribs 29 which are parallel and which are located above the guide track 19. More particularly, each stop rib 29 includes an upper stop surface 31 against which an upper face of the cuvettes strip 3 is adapted to bear when the cuvettes strip 3 is received in the guide element 18.

In addition, the drive device 17 includes a bearing device 32 which is located below the guide track 18 and more particularly between the lower and upper strands 23.1, 23.2 of the drive belt 23. The bearing device 32 is configured to exert a bearing force F against a belt portion 33 of the upper strand 23.2 of the drive belt 23 such that, when the cuvettes strip 3 is received in the guide element 18, the cuvettes 4 located opposite the belt portion are pressed by the belt portion against the upper stop surfaces 31 provided on the stop ribs 29.

More particularly, the bearing device 32 is configured such that the bearing force F exerted against the upper strand 23.2 of the drive belt 23 is directed transversely, and for example perpendicularly, to the guide track 18. Advantageously, the bearing force F is directed substantially vertically.

For example, the bearing device 32 may include a bearing pad 34 mounted movable according to a direction of displacement which is substantially vertical, and a drive member (not shown in the figures) configured to displace the bearing pad 34 vertically according to the direction of displacement. According to an embodiment of the invention, the bearing device 32 may further include a damping cushion 34.1, for example elastically deformable, disposed between the bearing pad 34 and the upper strand 23.2 of the drive belt 23.

The automatic analysis apparatus 2 also comprises a measuring station 35 disposed along the guide track 19. Advantageously, the bearing device 32 and the passage openings 28 are located at the measuring station 35.

According to the embodiment represented in the figures, the measuring station 35 includes several measuring units 36 shifted along the guide track 19, and for example five identical measuring units 36. More particularly, each of the measuring units 36 is configured to determine a coagulation time of a blood sample contained in a cuvette 4 of the cuvettes strip 3 that is located at said measuring unit 36. In addition, each measuring unit is configured to carry out absorbance, colorimetry and/or turbidimetry optical measurements. In particular, each measuring unit 36 is configured to measure the D-dimers or CRP content in the blood sample to be analyzed. Thus, the measuring units 36 according to the present invention are thus versatile.

Each measuring unit 36 comprises a magnetic field generation system 37 configured to generate a magnetic field adapted to displace a ferromagnetic bead 11, received in the cuvette 4 located at the respective measuring unit 36, along the raceway 9 and according to an oscillatory movement. Advantageously, the magnetic field generation system 37 of each measuring unit 36 includes two electromagnets 37.1, 37.2 disposed coaxially and located on either side of the guide track 19. Advantageously, the excitation frequency of the magnetic field generated by each magnetic field generation system 37 is close to the natural frequency of the oscillatory movement of a ferromagnetic bead 11.

According to an embodiment of the invention, each magnetic field generation system 37 includes a setting unit which is configured to set the durations of the current pulses applied to the respective two electromagnets according to the tests to be carried out on the blood sample contained in the cuvette 4 of the cuvettes strip 3 that is located at the respective measuring unit 36. Therefore, the different magnetic field generation systems 37 may be controlled independently of one another, and that in particular so as to set the exciting force applied by each of the respective electromagnets on the ferromagnetic bead 11 contained in the cuvette 4 located at the respective measuring unit 36. These arrangements allow, on the one hand, avoiding «breaking» the forming clot by limiting the oscillation frequency of the ferromagnetic bead 11 and, on the other hand, avoiding a stoppage of the ferromagnetic bead 11 (because of a high viscosity of the blood sample) before massive polymerization of the fibrinogen into fibrin, and therefore before the formation of the clot.

In addition, such a configuration of the different magnetic field generation systems 37 allows carrying tests of different kinds on the five measuring units 36, which is important in particular to carry out urgent tests where all of the tests prescribed for a patient must be performed rapidly.

Figure 6:
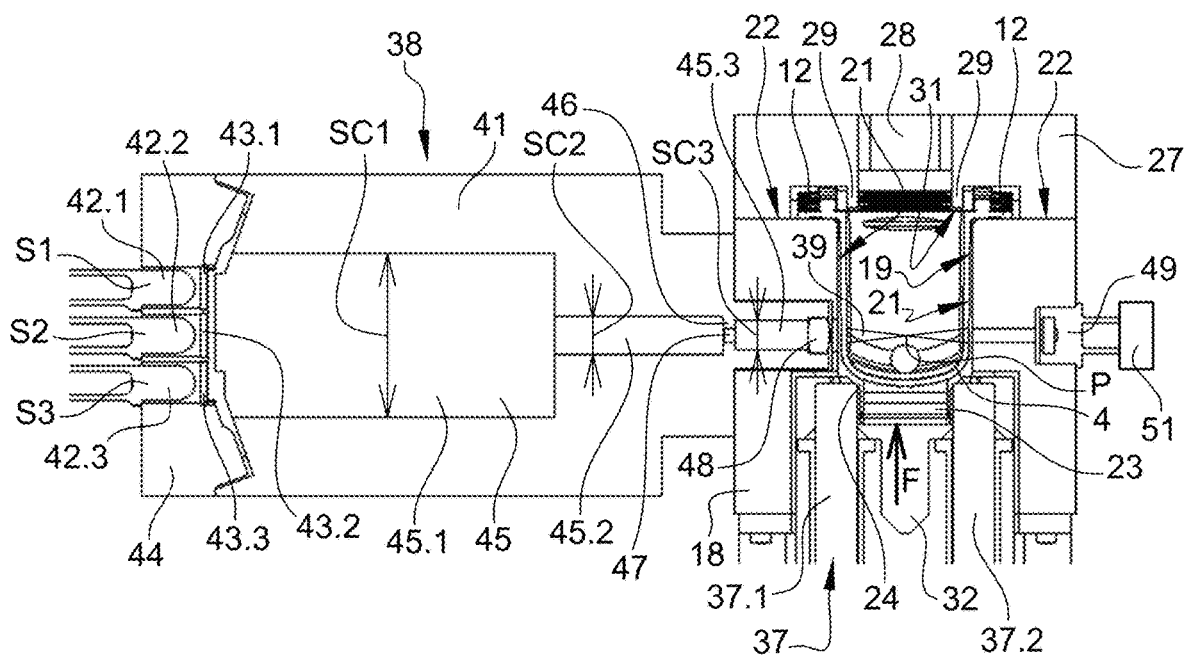
FIG. 6 is a cross-sectional view of the automatic analysis apparatus of FIG. 1.
Figure 7:
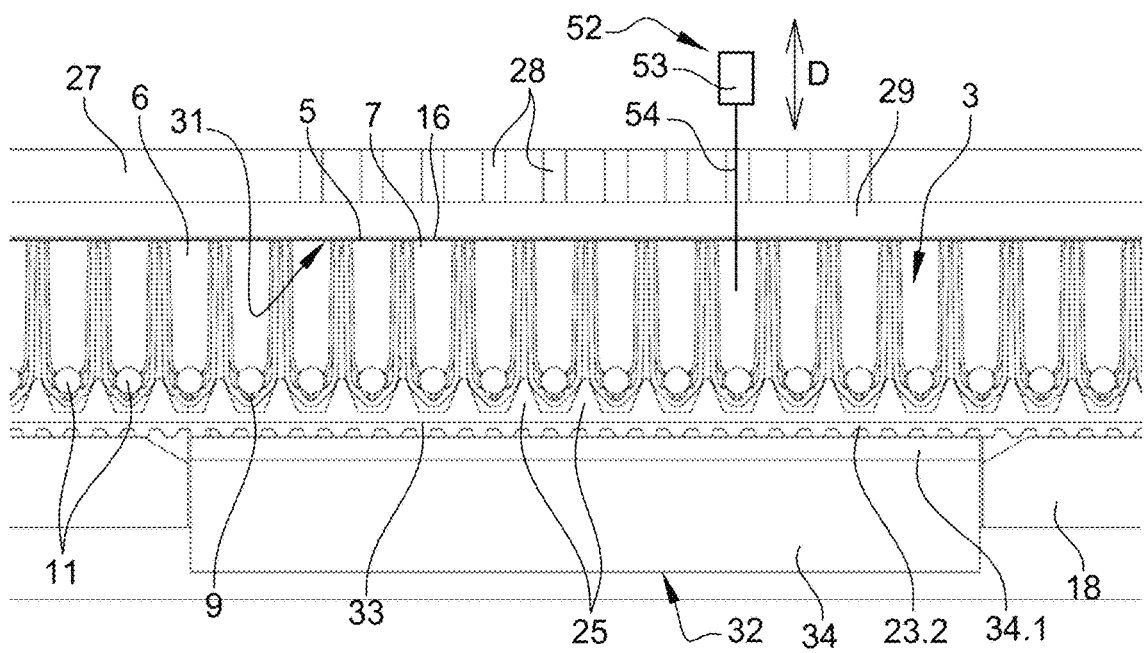
FIG. 7 is a partial longitudinal sectional view of the automatic analysis apparatus of FIG. 1.
Figure 8:
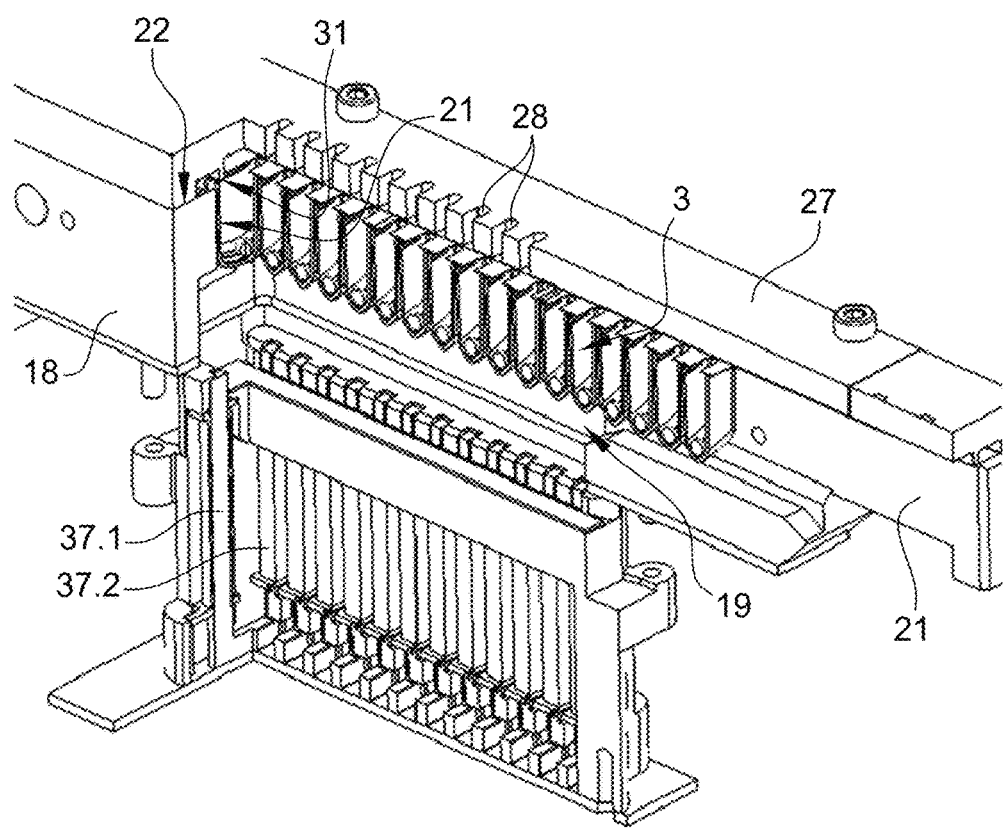
FIG. 8 is a perspective partial view, partially truncated, of the automatic analysis apparatus of FIG. 1.
Figure 9:
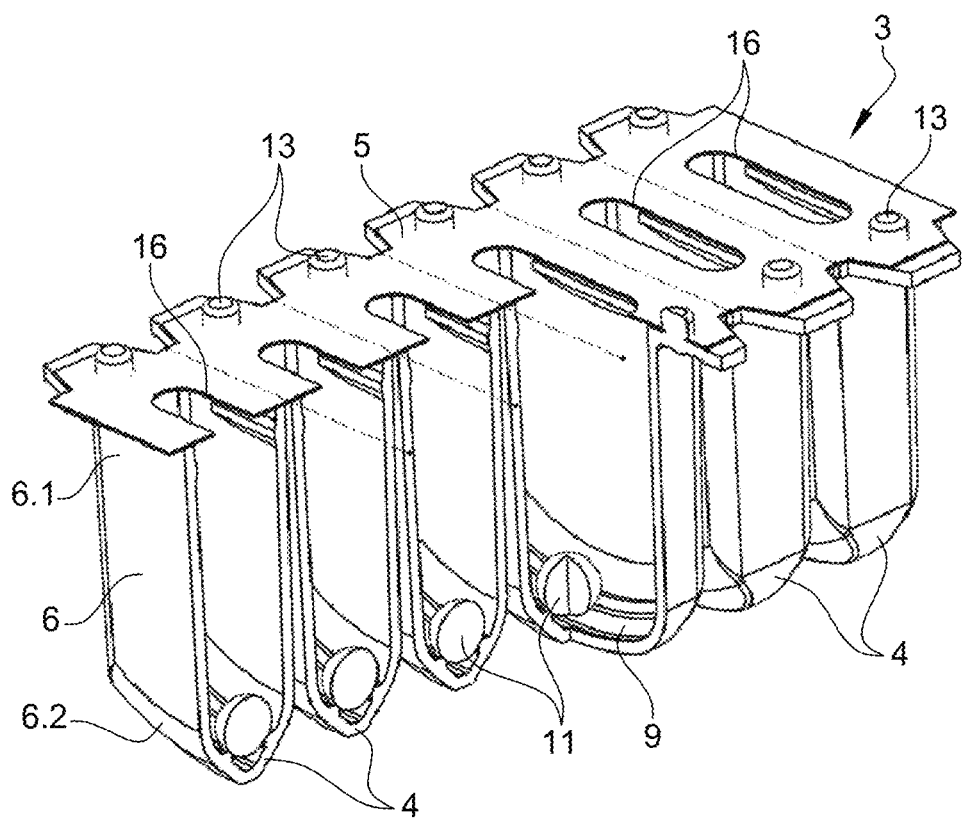
FIG. 9 is a perspective partial view, partially truncated, of a cuvettes strip of the automatic analysis apparatus of FIG. 1.
Figure 10:
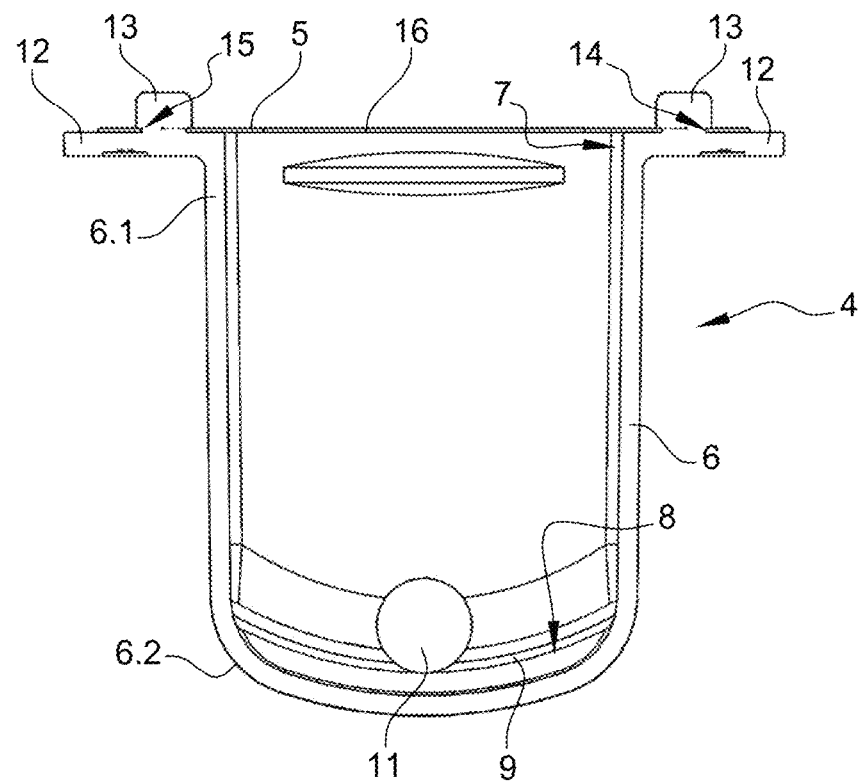
FIG. 10 is a sectional view of one cuvette of the cuvettes strip of FIG. 9.

As shown in FIG. 6, each measuring unit 36 also comprises an emission device 38 configured to emit an incident light beam 39 in the direction of the blood sample contained in the cuvette 4 located at the respective measuring unit 36. The incident light beam 39 is configured to be at least partially concealed by the ferromagnetic bead 11, contained in the cuvette 4 located at the respective measuring unit 36, over at least one portion of the movement of the ferromagnetic bead 11 along the raceway 9, and in particular when the ferromagnetic bead 11 is located at the ends of the raceway 9. Advantageously, each measuring unit 36 may be configured such that, when a cuvette 4 is located at said measuring unit 36 and when the ferromagnetic bead 11 received in said cuvette 4 lies at the lowest point of the raceway 9 of said cuvette 4, the ferromagnetic bead 11 does not conceal the incident light beam 39.

The emission device 38 of each measuring unit 36 includes a plurality of light sources S1, S2, S3, for example three, configured to emit monochromatic light beams with different wavelengths, and a wavelengths multiplexing device 41 configured to mix the light beams with different wavelengths originating from the light sources S1, S2, S3 so as to form a polychromatic light beam, and therefore such that the incident light beam 39 emitted by each emission device 38 is polychromatic.

As shown more particularly in FIG. 6, the light sources S1, S2, S3 are shifted vertically from one another, and have optical axes extending substantially horizontally. Advantageously, the light sources S1, S2, S3 are superimposed.

Advantageously, the first light source S1 is configured to emit a light beam having a wavelength of about 405 nanometers (such a value is more particularly suitable for coagulation time measurements and for colorimetry measurements), the second light source S2 is configured to emit a light beam having a wavelength of about 540 nanometers (such a value is more particularly suitable for turbidimetry measurements) and the third light source S3 is configured to emit a light beam having a wavelength of about 630 nanometers.

According to the embodiment represented in the figures, each light source S1, S2, S3 includes a light-emitting diode 42.1, 42.2, 42.3 and a spectral selection filter 43.1, 43.2, 43.3 disposed in front of the respective light-emitting diode 42.1, 42.2, 42.3. Advantageously, the spectral selection filters 43.1, 43.2, 43.3 of the different light sources S1, S2, S3 are substantially coplanar, and the light sources S1, S2, S3 are fastened to a support member 44.

As shown in FIG. 6, the wavelengths multiplexing device 41 includes an optical cavity 45 which is configured to collect the light beams with different wavelengths originating from the light sources S1, S2, S3, and to mix these light beams with different wavelengths. For example, the optical cavity 45 may have a length comprised between 40 and 70 mm, and advantageously between 45 and 60 mm.

The optical cavity 45 includes a first cavity portion 45.1 located in the proximity of the light sources S1, S2, S3 and having a first cross-section SC1 which is constant along the optical axis of the optical cavity 45, and a second cavity portion 45.2 located in the continuation of the first cavity portion 45.1 and having a second cross-section SC2 which is constant along the optical axis of the optical cavity 45 and which is smaller than the first cross-section SC1. Advantageously, the first cavity portion 45.1 and the second cavity portion 45.2 are disposed coaxially.

According to the embodiment represented in the figures, the first cross-section SC1 of the first cavity portion 45.1 is oblong and is directed substantially vertically, and the second cavity portion 45.2 is cylindrical and the second cross-section SC2 is circular. For example, the second cross-section SC2 of the second cavity portion 45.2 may have a diameter comprised between 2 and 4 mm.

According to the embodiment represented in the figures, the optical cavity 45 further includes a third cavity portion 45.3 which is separate from the second cavity portion 45.2 by a separating wall 46 including a passage orifice 47 having a section smaller than the second cross-section SC2. Advantageously, the first, second and third cavity portions 45.1, 45.2, 45.3 and the passage orifice 47 are disposed coaxially.

For example, the third cavity portion 45.3 may have a third cross-section SC3 which is circular and constant along the optical axis of the optical cavity 45. For example, the third cross-section SC3 may be substantially identical to or smaller than the second cross-section SC2.

The emission device 38 of each measuring unit 36 further includes a focusing lens 48, such as a biconvex focusing lens, which is located at the output of the respective wavelengths multiplexing device 41. For example, the focusing lens 48 may have a 3 mm diameter and have a 4.5 mm focal distance.

Advantageously, the focusing lens 48 of each emission device 38 is configured to collimate the polychromatic light beam originating from the respective wavelengths multiplexing device 41 and to focus the polychromatic light beam on a focus point P located in the guide track 19, and advantageously at the center of the cuvette 4 that is located at the respective measuring unit 36. The focus point P, where the polychromatic light beam is focused, is located in the lower portion 6.2 of the cuvette 4 that is located at the respective measuring unit 36, and for example above the respective ferromagnetic bead 11.

In particular, each emission device 38 is configured such that the portion of the incident light beam 39 extending in the guide track 19 is substantially symmetrical on either side of the focus point P. Advantageously, the incident light beam 39 has a diameter smaller than 0.5 mm at the focus point P, and a diameter smaller than 2 mm at the input and at the output of the biological fluid to be analyzed contained in the cuvette 4 located at the respective measuring unit 36.

Advantageously, the focusing lens 48 is positioned at a distance from the respective wavelengths multiplexing device 41 which substantially corresponds to the focal distance of the focusing lens 48. For example, a ratio between the focal distance of the focusing lens 48 and the distance between the respective wavelengths multiplexing device 41 and the focusing lens 48 may be comprised between 0.8 and 1.2, and advantageously between 0.8 and 1.

As shown in FIG. 6, the emission device 38 of each measuring unit 36 is configured so that each light beam originating from a light source S1, S2, S3 propagates in free space from the corresponding light source up to the collimating lens 48.

Each measuring unit 36 further comprises a detection element 49 configured to detect at least one light beam that is transmitted through the cuvette 4 located at the respective measuring unit 36 and which is derived from the incident light beam 39 emitted by the respective emission device 38, and to output a measurement signal. For example, the detection element 49 may be a photodetector, such as a photodiode.

Advantageously, the detection element 49 is located substantially in the optical axis of the incident light beam 39 emitted by the respective emission device 38. Thus, the emission device 38 and the detection element 49 of the same measuring unit 36 are disposed on either side of the guide track 19, and more particularly on either side of the lateral guide walls 21 of the guide element 18. Hence, the emission device 38 and the detection element 49 of the same measuring unit 36 are configured to be disposed on either side of the cuvettes strip 3 when the cuvettes strip 3 is received in the guide element 18.

In addition, the emission device 38 and the detection element 49 of the same measuring unit 36 are configured so as to be disposed substantially in the axis of the raceway 9 of the cuvette 4 of the cuvettes strip 3 that is located at the respective measuring unit 36.

Each measuring unit 36 further includes a processing unit 51 configured to:
  carry out a processing of each measurement signal provided by the respective detection element 49 so as to provide a signal representative of the variation of at least one physical quantity representative of the movement of the ferromagnetic bead 11 contained in the cuvette 4 located at the respective measuring unit 36, the at least one physical quantity representative of the movement of the ferromagnetic bead 11 being for example the amplitude and/or the frequency of the movement of the ferromagnetic bead, and
  determine a value of the coagulation time of the blood sample contained in the cuvette 4 located at the respective measuring unit 36, from the signal representative of the variation of at least one physical quantity representative of the movement of the ferromagnetic bead 11.

The processing unit 51 may also be configured to carry out an additional processing of each measurement signal provided by the respective detection element 49 so as to provide a signal representative of the variation of at least one optical property of the blood sample to be analyzed contained in the cuvette 4 located at the respective measuring unit 36, and in particular of the variation of the absorbance of said blood sample to be analyzed.

Thus, the processing unit 51 of each measuring unit 36 may be configured to synchronously measure:
- a first value of the coagulation time of the blood sample which is obtained by timekeeping between the time of injection of the triggering reagent and the decrease in the mechanical amplitude of the movement of the ferromagnetic bead 11 due to the generation of a fibrin network corresponding to the polymerization of fibrinogen,
- a second value of the coagulation time of the blood sample which is obtained by timekeeping between the time of injection of the triggering reagent and the decrease in the optical transmittance of the reactive medium due to the generation of a fibrin network corresponding to the polymerization of fibrinogen.

Furthermore, each measuring unit 36 allows measuring, with the same means, the optical density of the blood sample in order to determine concentrations according to Beer Lambert law, or according to more complex laws for immunochemistry reactions measured in turbidimetry.

According to a variant of the invention, the different processing units 51 may be formed by the same electronic microcontroller.

In addition, the automatic analysis apparatus 2 comprises a sampling device 52 (cf. FIGS. 1 and 7) including a sampling head 53 equipped with a sampling needle 54. The sampling device 52 further comprises displacement means arranged so as to displace the sampling head 53 in translation along a substantially vertical direction D. According to the embodiment represented in the figures, the sampling head 54 is housed within a support case 55 which is rotatably mounted about a vertical axis.

The automatic analysis apparatus 2 further comprises:
- a first loading rotor 56 mounted movable in rotation about a first axis of rotation which is substantially vertical, the first loading rotor 56 comprising a plurality of housings adapted to receive vessels containing samples of a biological liquid to be analyzed, and
- a second loading rotor 57 mounted movable in rotation about a second axis of rotation which is substantially vertical, the second loading rotor 57 comprising a plurality of housings adapted to receive vessels containing reagent products.

More particularly, the sampling device 52 is configured to sample biological liquid samples to be analyzed contained in vessels received in the first loading rotor 56, and to sample reagent products contained in vessels received in the second loading rotor 57.

In addition, the sampling device 52 is configured to feed the cuvettes 4 located opposite the passage openings 28 provided on the covering element 27 with biological liquid samples to be analyzed and/or with reagent products originating from the first and second loading rotors 56, 57. In particular, the sampling needle 54 of the sampling device 52 is adapted to extend through a passage opening 28 and to penetrate into the receptacle 6 of the cuvette 4 located opposite the passage opening 28.

According to a variant of the automatic analysis apparatus 2, the vessels containing biological liquid samples to be analyzed and the vessels containing reagent products may be received in the same loading rotor.

The automatic analysis apparatus 2 may further comprise a rinse well (not shown in the figures) adapted to receive and rinse the sampling needle 54 of the sampling head 53.

The automatic analysis apparatus 2 may further comprise a separation and storage station 58 which is located downstream of the measuring station 35, and advantageously at one end of the guide element 18, and which is configured to separate the used cuvettes from one another and to store the separated used cuvettes. In particular, the separation and storage station 58 may include a cutter member configured to cut the film between two adjacent used cuvettes, and a collecting bin configured to store the separated used cuvettes. Advantageously, the cutter member of the separation and storage station 58 is not actuated when measurements are carried out in one of the measuring units 36, in order not to disturb these measurements.

The automatic analysis apparatus 2 also comprises a control unit 59 configured to control the operation of the drive device 17, and in particular of the drive motor of the drive belt 23, of the sampling device 52, and of the emission device 38, of the detection element 49 and of the magnetic field generation system 37 of each measuring unit 36.

In particular, the control unit 59 is programmed so as to control pipetting sequences suited to the nature of the analyses to be performed, and which may successively comprise:
- prior rinsing of the sampling needle 54,
- sampling of a dose of a blood sample to be analyzed contained in one of the vessels of the first loading rotor,
- injection of this dose in a cuvette 4 located at a passage opening 28,
- rinsing of the sampling needle 54,
- sampling of a dose of a reagent contained in one of the vessels of the second loading rotor,
- injection of this reagent dose in the aforementioned cuvette 4.

The control unit 59 is also programmed to displace the cuvettes strip 3 so as to bring a cuvette 4, containing a blood sample to be analyzed and one or several reagent(s), at a measuring unit 36, in order to determine for example the coagulation time of the blood sample.

The cooperation of the drive belt 23 with the lower portions 6.2 of the cuvettes 4 allows ensuring an accurate horizontal positioning of the lower portions 6.2 of the cuvettes 4 at each measuring unit 36, whereas the presence of the upper stop surfaces 31 and of the bearing device 32 allows reducing the vertical mechanical clearance of the cuvettes by sandwiching the cuvettes strip 3 between the drive belt 23 and the upper stop surfaces 31, which ensures an accurate vertical positioning of the lower portions 6.2 of the cuvettes 4 at each measuring unit 36.

Furthermore, the drive device 17 according to the present invention allows mechanically uncoupling the cuvettes 4 from one another and mechanically stabilizing the cuvettes 4 at the measuring units 36, such that the introduction of the sampling needle 54 into one of the cuvettes 4, in order to feed said cuvette with the biological fluid to be analyzed or with reagents, is not likely to cause vibrations in the adjacent cuvettes 4.

Consequently, the drive device 17 according to the present invention allows significantly improving the reliability of the measurements carried out with the automatic analysis apparatus 2 according to the present invention.

The configuration of the drive belt 23 also allows disposing the emission device 38 and the detection element 49 of each measuring unit 36 on either side of the guide track 19, which allows limiting the vertical bulk of the drive device 17.

In addition, the specific configuration of each emission device 38 allows carrying out very accurate absorbance and turbidimetry optical measurements even in the presence of the ferromagnetic bead 11, which allows substantially increasing the analytic performances of some immunoturbidimetric tests. The narrow collimation and the focusing of the incident light beam 39 also allows improving the measuring range in turbidimetry.

It goes without saying that the invention is not limited to the sole embodiment of this automatic analysis apparatus 2 for in vitro diagnostics, described hereinabove as example, but it encompasses, on the contrary, all variants thereof.

What is claimed is:

1. An automatic analysis apparatus for in vitro diagnostics, including:
   a cuvettes strip including a plurality of cuvettes which are secured together by a film which is flexible, each cuvette of the plurality of cuvettes comprising a receptacle configured to contain a biological fluid to be analyzed, the receptacle of each cuvette of the plurality of cuvettes comprising an upper portion including an upper opening and a lower portion including a bottom delimiting a concave guiding path whose concavity is directed upwards, the film being secured to the upper portion of the receptacle of each cuvette of the plurality of cuvettes,
   a measuring station configured to determine times for modification of a physical state of a biological fluid to be analyzed contained in a cuvette of the cuvettes strip, and
   a drive device, the drive device including:
   a guide element defining a guide track along which the measuring station is disposed, the cuvettes strip being received in the guide element and the guide element being configured to guide the cuvettes strip in translation along the guide track, and
   a drive belt driven by a rotary support member, the drive belt being configured to displace the cuvettes strip in translation along the guide track, the drive belt including outer projections which are spaced apart along the drive belt,
   wherein the drive belt is disposed below the guide track and the outer projections of the drive belt cooperating with lower portions of the receptacles of the cuvettes strip received in the guide element, each outer projection, among said outer projections which cooperates with lower portions of the receptacles, extending between the lower portions of two adjacent receptacles of the cuvettes strip received in the guide element; and
   wherein the drive device includes at least one upper stop surface which is located above the guide track, and a pushing device which is located below the guide track and which exerts a pushing force against a belt portion of the drive belt such that the cuvettes located above the belt portion are pressed by the belt portion against the at least one upper stop surface.

2. The automatic analysis apparatus according to claim 1, further comprising another rotary support member, the rotary support member and the another rotary support member configured to support the drive belt, the rotary support member and the another rotary support member having axes of rotation which extend substantially horizontally.

3. The automatic analysis apparatus according to claim 1, wherein the guide element includes a lower opening emerging in the guide track and through which an upper strand of the drive belt extends.

4. The automatic analysis apparatus according to claim 1, wherein the drive device includes a covering element which is fastened to the guide element and which covers the receptacles of the cuvettes strip.

5. The automatic analysis apparatus according to claim 1, wherein the measuring station includes at least one measuring unit configured to determine a coagulation time of a blood sample contained in a cuvette of the cuvettes strip that is located at the at least one measuring unit, the at least one measuring unit comprising:
   a magnetic field generation system configured to generate a magnetic field adapted to displace a ferromagnetic bead, received in the receptacle of the cuvette located at the at least one measuring unit, along the respective concave guiding path and according to an oscillatory movement,
   an emission device configured to emit an incident light beam in a direction of the blood sample contained in the cuvette located at the at least one measuring unit, the incident light beam being configured to be at least partially concealed by the ferromagnetic bead over at least one portion of the movement of the ferromagnetic bead along the guiding path, and
   a detection element configured to detect at least one light beam that is transmitted through the cuvette located at the at least one measuring unit and which is derived from the incident light beam, and to output a measurement signal.

6. The automatic analysis apparatus according to claim 5, wherein the emission device and the detection element are disposed on either side of the guide track.

7. The automatic analysis apparatus according to claim 5, wherein the emission device includes:
   a plurality of light sources configured to emit light beams with different wavelengths, and
   a wavelengths multiplexing device which includes an optical cavity including a first cavity portion located in the proximity of the light sources and having a first cross-section, and a second cavity portion located in a continuation of the first cavity portion and having a second cross-section which is smaller than the first cross-section, the wavelengths multiplexing device being configured to mix the light beams with different wavelengths originating from the light sources, through reflection of the light beams on inner surfaces of the optical cavity, so as to form a polychromatic light beam.

8. The automatic analysis apparatus according to claim 7, wherein each light source includes a light-emitting diode and a spectral selection filter disposed in front of the respective light-emitting diode.

9. The automatic analysis apparatus according to claim 7, wherein the second cavity portion is cylindrical.

10. The automatic analysis apparatus according to claim 7, wherein the emission device further includes a focusing lens configured to focus the polychromatic light beam on a focus point located in the guide track.

11. The automatic analysis apparatus according to claim 2, wherein the guide element includes a lower opening emerging in the guide track and through which an upper strand of the drive belt extends.

12. The automatic analysis apparatus according to claim 5, wherein the incident light beam emitted by the emission device is a polychromatic light beam.

* * * * *